US00PP24715P3

(12) United States Plant Patent
Dibley

(10) Patent No.: US PP24,715 P3
(45) Date of Patent: Jul. 29, 2014

(54) ***STREPTOCARPUS* PLANT NAMED 'SLSBV08-0'**

(50) Latin Name: ***Streptocarpus* hybrid**
Varietal Denomination: SLSBV08-0

(71) Applicant: Lynne Dibley, Ruthin (GB)

(72) Inventor: Lynne Dibley, Ruthin (GB)

(73) Assignee: Dibleys Nurseries (GB)

( * ) Notice: Subject to any disclaimer, the term of this patent is extended or adjusted under 35 U.S.C. 154(b) by 0 days.

(21) Appl. No.: 13/694,740

(22) Filed: Dec. 27, 2012

(65) Prior Publication Data

US 2014/0189919 P1 Jul. 3, 2014

(51) Int. Cl.
*A01H 5/00* (2006.01)

(52) U.S. Cl.
USPC ..... Plt./333

(58) Field of Classification Search
USPC ..... Plt./333
See application file for complete search history.

*Primary Examiner* — Anne Grunberg
(74) *Attorney, Agent, or Firm* — Cassandra Bright

(57) ABSTRACT

A new and distinct *Streptocarpus* cultivar named 'GFB0244' is disclosed, characterized by large flowers which are heavily veined on lower 3 lobes and multi-flowering, 6-8 per inflorescence. The new variety is a *Streptocarpus*, suitable as an outdoor garden or container plant.

2 Drawing Sheets

Figure 1:
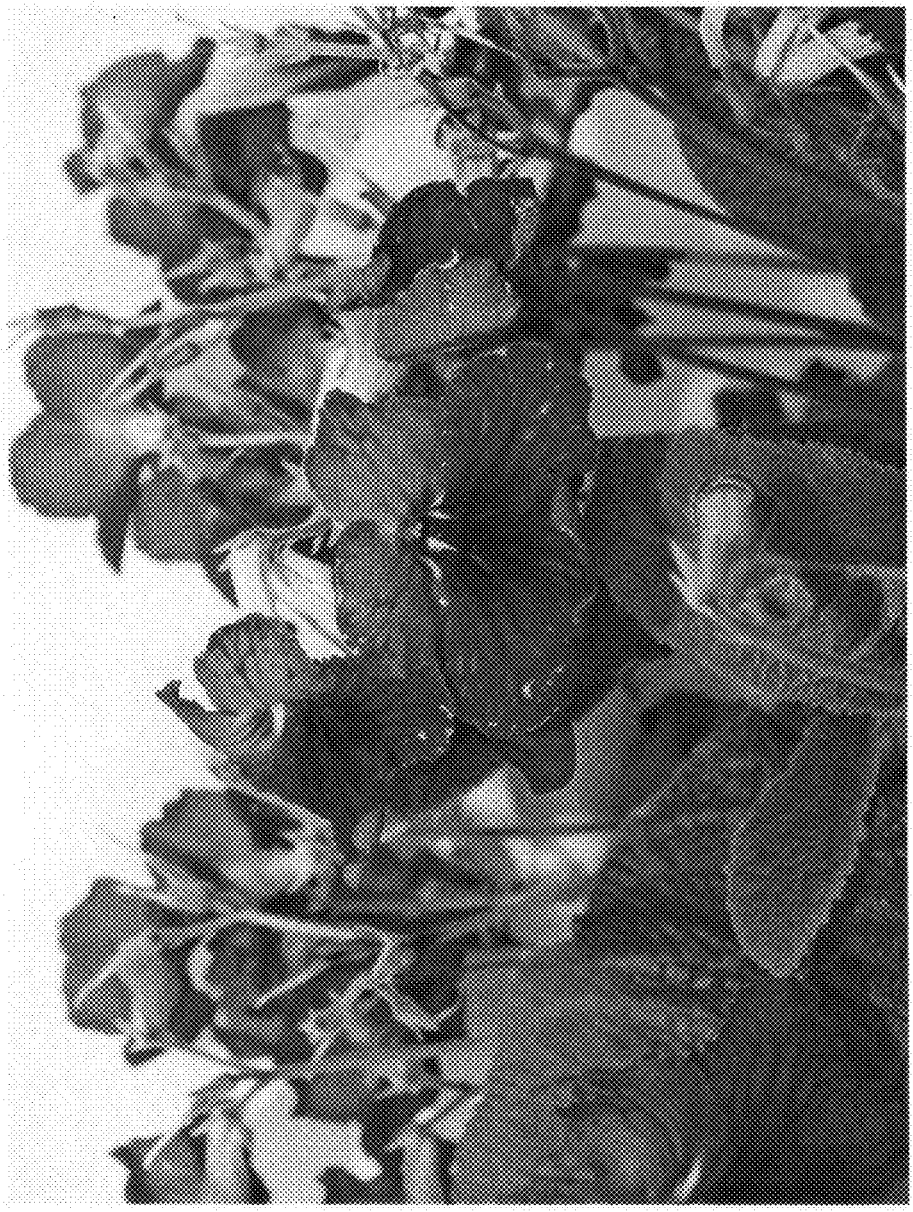

Latin name of the genus and species: *Streptocarpus* hybrid.
Variety denomination: 'SLSBV08-0'.

The new *Streptocarpus* cultivar is the product of a planned breeding program by the inventor Lynne Dibley, a citizen of the United Kingdom. The breeding program was carried out in Llanelidan, Ruthin, the United Kingdom. The objective of the breeding program was to develop new *Streptocarpus* varieties for ornamental purposes.

The new variety resulted from the crossing of the seed parent, an unnamed, unpatented proprietary *Streptocarpus* seedling with the pollen parent, an unnamed, unpatented proprietary *Streptocarpus* seedling in 2008. The new variety was discovered in 2009 by the inventor in a group of seedlings resulting from the 2008 crossing, at a commercial nursery in Ruthin, United Kingdom.

Asexual reproduction of the new cultivar 'SLSBV08-0' by vegetative cuttings was first performed at a commercial greenhouse in Llanelidan, Ruthin, the United Kingdom during 2009. Subsequently at least five generations have been produced from vegetative cuttings, and have shown that the unique features of this cultivar are stable and reproduced true to type. After observing the new variety confidentially over multiple seasons, the variety was also propagated in tissue culture, in a controlled laboratory, without access by third parties.

SUMMARY OF THE INVENTION

The cultivar 'SLSBV08-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'SLSBV08-0'. These characteristics in combination distinguish 'SLSBV08-0' as a new and distinct *Streptocarpus* cultivar:

1. Large flowers
2. Heavily veined lower floral lobes.
3. Distinctive high flower count per inflorescence.

COMPARISON TO THE PARENT VARIETIES

Plants of the new cultivar 'SLSBV08-0' are similar in most horticultural characteristics to plants of the unnamed, unpatented proprietary seed parent. However, the new variety produces larger flower and leaves than the seed parent. Additionally, 'SLSBV08-0' produces a darker colored flower than the seed parent.

Plants of the new cultivar 'SLSBV08-0' are similar in most horticultural characteristics to plants of the unnamed, unpatented proprietary pollen parent. However, the new variety flowers earlier and produces a smaller flower than the pollen parent. Additionally, plants of 'SLSBV08-0' produce flowers of a different color than the pollen parent.

COMPARISON TO COMMERCIAL VARIETY

The new cultivar can be compared to the commercial variety *Streptocarpus* 'Amanda', unpatented. Plants of the two cultivars are similar in most horticultural characteristics, however, plants of 'SLSBV08-0' produce a darker colored flower, smaller, more abundant leaves. And flower earlier on a shorter peduncle than 'Amanda'. The new variety can also be compared to *Streptocarpus* 'Bethan', unpatented. The varieties are quite similar however, plants of the new variety produce larger, darker flowers on a longer peduncle than produced by plants of 'Bethan'.

BRIEF DESCRIPTION OF THE PHOTOGRAPHS

The accompanying photograph in FIG. 1 illustrates in full color a typical flower of 'SLSBV08-0'.

Figure 2:
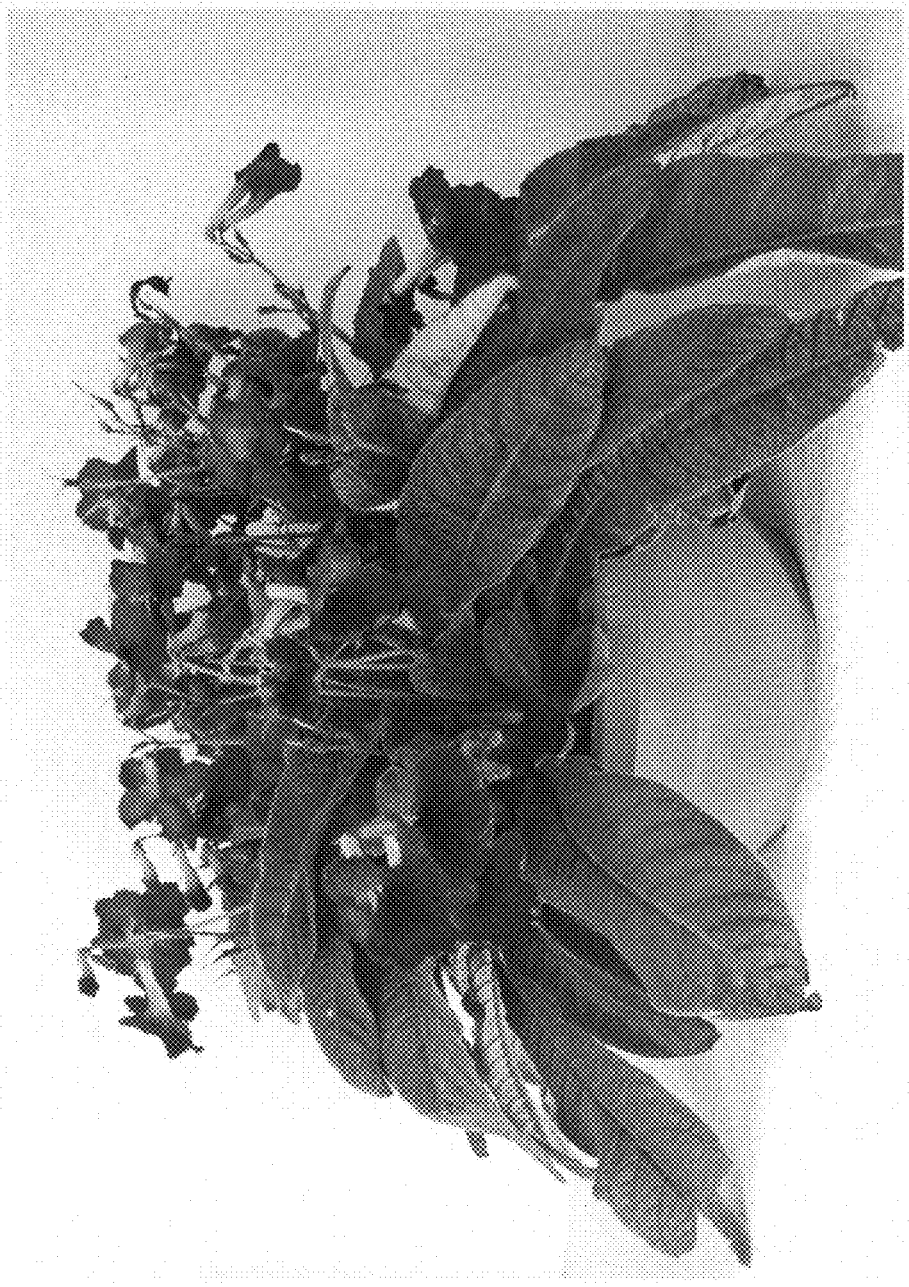

FIG. 2 illustrates a typical plant of 'SLSBV08-0' grown in a greenhouse, in a 12 inch commercial pot. Age of the plant photographed is approximately 30 weeks from a rooted plantlet. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurement describe 'SLSBV08-0' plants grown in a commercial greenhouse in Oxnard, Calif. The growing temperature ranged from approximately 12° C. to 30° C. The greenhouse is subject to partial shade. General light conditions are bright, normal sunlight with some shade during the brightest part of the day. Measurements and numerical values represent averages of typical plant types.

Botanical classification: *Streptocarpus* hybrid 'SLSBV08-0'.

PROPAGATION

Time to initiate roots: About 20 to 25 days at approximately 21 to 25° C.

Root description: Fine, fibrous.

PLANT

Growth habit: Upright.

Age of the plant described: Approximately 30 weeks from a well rooted plantlet.

Pot size of plant described: 12 inch pot.

Height: Approximately 18 cm from soil line to top of foliar plane. Approximately 25 cm to top of highest flower.

Plant spread: Approximately 50 cm at widest point.

Growth rate: Moderate.

Branching characteristics: Basal rosettes of foliate, no stem, no branches.

FOLIAGE

Leaf:

- *Arrangement*.—Rosette.
- *Quantity*.—Average 50 to 65 leaves.
- *Average length*.—Approximately 24 cm.
- *Average width*.—Approximately 7 cm.
- *Shape of blade*.—Lanceolate.
- *Apex*.—Acute.
- *Base*.—Attenuate.
- *Margin*.—Crenate.
- *Appearance of top surface*.—Matte.
- *Appearance of bottom surface*.—Matte.
- *Pubescence*.—Very short, less than 1 mm hairs, densely covering top and bottom leaf surfaces.
- *Aspect*.—Somewhat undulating, overall leaf reflexes downward in older foliage.
- *Color*.—Young foliage upper side: Near RHS Green 137A. Young foliage under side: Near RHS Green 138B. Mature foliage upper side: Near RHS Green 137B. Mature foliage under side: Near RHS Green 138C.
- *Venation*.—Type: Pinnate. Venation color upper side: Near RHS Green 143C. Venation color under side: Near RHS Green 138D.
- *Petiole*.—Not present, leaves sessile.

FLOWER

Natural flowering season: Continuous.

Inflorescence and flower type and habit: Racemes of 4 to 8 asymmetrical funnel shaped flowers.

Inflorescence longevity on plant: At least 2 weeks before any significant change is observed.

Approximate quantity of flowers per plant: Approximately 40 mature and immature flowers per plant.

Flowers persistent:

Inflorescence:

- *Diameter of entire inflorescence*.—Approximately 10.0 cm.
- *Depth of inflorescence*.—Approximately 8.0 cm.

Individual flower bud:

- *Shape*.—Tubular, with spherical apex.
- *Length*.—Approximately 3.8 cm.
- *Diameter*.—Approximately 1.4 cm.
- *Color*.—Near RHS Violet-Blue 92C, apex Violet-Blue N189C.

Flowers:

- *Flower length*.—6.0 cm.
- *Flower width*.—5.5 cm.
- *Upper petals* (*upper lip*).—Number: 2, fused together at base. Length: 3.0 cm. Width: 2.4 cm. Shape: Obicular. Apex: Obtuse, ruffled. Margin: Shallow crenate. Texture: Velvety, all surfaces. Pubescent outer surface. Color: When opening: Inner surface: Background color RHS Violet-Blue N89C. Very lightly veined coloration Violet-Blue N89A. Outer surface: RHS Violet 86B. Fully opened: Inner surface: Background color RHS Violet-Blue N89C. Lightly veined coloration Violet-Blue N89A. Outer surface: RHS Violet 86B. Aging: Inner surface: Near RHS Violet-Blue N92C. Outer surface: Near RHS Violet 83B.
- *Lower petals* (*lower lip*).—Quantity: 3. Length: 2.5 cm. Width: 2.5 cm. Shape: Orbicular, fused at base. Apex shape: Obtuse. Margin: Shallow crenate, undulating. Texture: Velvety, all surfaces. Pubescent outer surface. Color: When opening: Inner surface: Background color RHS Violet-Blue N89C. Heavily veined coloration Violet-Blue N89A. Outer surface: RHS Violet 86B. Fully opened: Inner surface: Background color RHS Violet-Blue N89C. Heavily veined coloration Violet-Blue N89A. Outer surface: RHS Violet 86B. Aging: Inner surface: Background color RHS Violet-Blue N88A. Heavily veined coloration Violet-Blue N92A. Outer surface: RHS Violet 87A.
- *Throat*.—Length: 3.0 cm. Width: 1 cm, at widest point. Texture: glabrous, shiny inner surface. Outer surface pubescent. Color: When opening: Inner surface: RHS White N155A infrequent stripe Purple N79A. Outer surface: RHS White N155A with flush Violet 86C. Fully opened: Inner surface: RHS White N155A infrequent stripe Purple N79A. Outer surface: RHS White N155A with flush Violet 86C. Aging: Inner surface: RHS White N155A with stripes Purple N79A. Outer surface: RHS White N155A with flush Violet 86C.

Sepals:

- *Quantity*.—Average 5.
- *Shape*.—Narrow deltate, base fused.
- *Length*.—Approximately 0.8 cm.
- *Width*.—Approximately 0.25 cm.
- *Apex*.—Acute.

*Base*.—Fused.
*Margin*.—Entire.
*Texture*.—Highly pubescent, all surfaces.
*Color*.—Upper Surface: Near RHS Green 137A. Lower Surface: Near RHS Green 137A.

Peduncle:
*Length*.—Longest average 17 cm. Shortest average 8 cm.
*Diameter*.—Approximately 0.4 cm.
*Texture*.—Densely pubescent.
*Color*.—Near RHS Yellow-Green 144B.
*Orientation*.—Approximately 90 to 75 degree angle from rosette Moderate outward curvature on peduncles emerging farther from center.

Pedicel:
*Length*.—Average range 0.8 cm to 1.8 cm.
*Diameter*.—Approximately 0.3 cm.
*Texture*.—Soft, dense pubescence.
*Color*.—Near RHS Yellow-Green 144B.
*Orientation*.—Approximately 30 degree angle from peduncle. Straight, or slightly outwardly curved.

Fragrance: None.

REPRODUCTIVE ORGANS

Stamens:
*Number*.—2.
*Filament length*.—Approximately 0.5 cm, unfused section.

Anthers:
*Length*.—Approximately 0.2 cm.
*Shape*.—Bi-lobed.
*Color*.—Near RHS White 155B.
*Pollen*.—Not observed.

Pistil:
*Number*.—1.
*Length*.—Approximately 2.3 cm.
*Style*.—Length: Approximately 2.0 cm. Color: Near RHS Greyed-Orange 177A from base to approximately 50% of length. Upper 50% near White N155C.
*Stigma*.—Shape: Bifurcate. Color: Near RHS White N155C.

OTHER CHARACTERISTICS

Seeds and fruits: Not observed.
Disease/pest resistance: Neither resistant nor susceptible to normal diseases and pests of *Streptocarpus*.
Temperature tolerance: USDA zones 9 to 11.

What is claimed is:

1. A new and distinct cultivar of *Streptocarpus* plant named 'SLSBV08-0' as herein illustrated and described.

* * * * *